(12) United States Patent
Copa et al.

(10) Patent No.: US 7,717,928 B2
(45) Date of Patent: May 18, 2010

(54) ANASTOMOSIS DEVICE CONFIGURATIONS AND METHODS

(75) Inventors: Vincent G. Copa, Minnetonka, MN (US); Kory P. Hamel, Bloomington, MN (US); Sidney F. Hauschild, St. Paul, MN (US); Suranjan Roychowdhury, Plymouth, MN (US); Robert L. Rykhus, Edina, MN (US)

(73) Assignee: AMS Research Corporation, Minnetonka, MN (US)

( * ) Notice: Subject to any disclaimer, the term of this patent is extended or adjusted under 35 U.S.C. 154(b) by 837 days.

(21) Appl. No.: 11/437,963

(22) Filed: May 19, 2006

(65) Prior Publication Data

US 2006/0276811 A1    Dec. 7, 2006

Related U.S. Application Data

(60) Provisional application No. 60/682,944, filed on May 20, 2005.

(51) Int. Cl.
*A61B 17/08* (2006.01)

(52) U.S. Cl. .......................................... 606/153; 606/1
(58) Field of Classification Search ................. 606/153
See application file for complete search history.

(56) References Cited

U.S. PATENT DOCUMENTS

| | | | | |
|---|---|---|---|---|
| 1,411,175 A | * | 3/1922 | Maguire | 294/149 |
| 1,803,048 A | * | 4/1931 | Allen | 119/819 |
| 2,966,905 A | * | 1/1961 | Kamenshine | 601/34 |
| 3,196,870 A | * | 7/1965 | Sprecher et al. | 128/877 |
| 3,640,273 A | * | 2/1972 | Ray | 602/5 |
| 3,947,927 A | * | 4/1976 | Rosenthal | 24/306 |
| 3,994,048 A | * | 11/1976 | Rosenthal | 24/306 |

(Continued)

FOREIGN PATENT DOCUMENTS

WO    WO 92/04869    4/1992

(Continued)

OTHER PUBLICATIONS

Igel et al., "Comparison of Techniques for Vesicourethral Anastomosis: Simple Direct Versus Modified Vest Traction Sutures," Urology, vol. XXXI, No. 6, pp. 474-477 (Jun. 1988).

(Continued)

*Primary Examiner*—(Jackie) Tan-Uyen T Ho
*Assistant Examiner*—Son Dang
(74) *Attorney, Agent, or Firm*—Jose' W. Jimenez; Kimberly K. Baxter; Gregory L. Koeller

(57) ABSTRACT

A surgical tool which comprises an elongated body having a proximal end and a distal end, first and second sets of tissue approximating structures having deployed and retracted positions relative to the elongated body, an actuating mechanism extending from the proximal end of the elongated body for independently deploying and retracting each of the first and second sets of tissue approximating structures, a drainage lumen extending from a drainage aperture at the distal end of the elongated body to the proximal end, a main balloon adjacent to the distal end of the elongated body, and a strap connector extending from the elongated body that is connectable with a stabilization strap.

4 Claims, 14 Drawing Sheets

U.S. PATENT DOCUMENTS

| | | | |
|---|---|---|---|
| 4,701,162 A | 10/1987 | Rosenberg | |
| 4,705,502 A | 11/1987 | Patel | |
| 4,792,330 A | 12/1988 | Lazarus et al. | |
| 4,848,367 A | 7/1989 | Avant et al. | |
| 4,873,977 A | 10/1989 | Avant et al. | |
| 4,909,785 A | 3/1990 | Burton et al. | |
| 4,911,164 A | 3/1990 | Roth | |
| 4,932,956 A | 6/1990 | Reddy et al. | |
| 5,047,039 A | 9/1991 | Avant et al. | |
| 5,123,908 A | 6/1992 | Chen | |
| 5,152,772 A | 10/1992 | Sewell, Jr. | |
| 5,211,649 A * | 5/1993 | Kohler et al. | 606/139 |
| 5,540,701 A | 7/1996 | Sharkey et al. | |
| 5,545,171 A | 8/1996 | Sharkey et al. | |
| 5,582,337 A * | 12/1996 | McPherson et al. | 224/660 |
| 5,695,504 A | 12/1997 | Gifford, III et al. | |
| 5,707,380 A | 1/1998 | Hinchliffe et al. | |
| 5,833,698 A | 11/1998 | Hinchliffe et al. | |
| 5,931,842 A | 8/1999 | Goldsteen et al. | |
| 5,964,791 A | 10/1999 | Bolmsjo | |
| 6,024,748 A | 2/2000 | Manzo et al. | |
| 6,119,045 A | 9/2000 | Bolmsjo | |
| 6,138,882 A * | 10/2000 | Buettner | 224/250 |
| 6,149,667 A | 11/2000 | Hovland et al. | |
| 6,193,734 B1 | 2/2001 | Bolduc et al. | |
| 6,238,368 B1 | 5/2001 | Devonec | |
| 6,254,570 B1 | 7/2001 | Rutner et al. | |
| 6,299,598 B1 | 10/2001 | Bander | |
| 6,302,905 B1 | 10/2001 | Goldsteen et al. | |
| 6,391,039 B1 | 5/2002 | Nicholas et al. | |
| 6,416,545 B1 | 7/2002 | Mikus et al. | |
| 6,440,146 B2 | 8/2002 | Nicholas et al. | |
| 6,447,533 B1 | 9/2002 | Adams | |
| 6,461,367 B1 | 10/2002 | Kirsch et al. | |
| 6,485,496 B1 | 11/2002 | Suyker et al. | |
| 6,494,908 B1 | 12/2002 | Huxel et al. | |
| 6,520,974 B2 | 2/2003 | Tanner et al. | |
| 6,530,932 B1 | 3/2003 | Swayze et al. | |
| 6,562,024 B2 | 5/2003 | Alvarez de Toledo et al. | |
| 6,565,579 B2 | 5/2003 | Kirsch et al. | |
| 6,602,243 B2 | 8/2003 | Noda | |
| 6,676,674 B1 * | 1/2004 | Dudai | 606/151 |
| 6,695,832 B2 | 2/2004 | Schon et al. | |
| 6,702,825 B2 | 3/2004 | Frazier et al. | |
| 6,719,709 B2 * | 4/2004 | Whalen et al. | 600/587 |
| 6,719,749 B1 | 4/2004 | Schweikert et al. | |
| 6,726,697 B2 | 4/2004 | Nicholas et al. | |
| 6,740,098 B2 | 5/2004 | Abrams et al. | |
| 6,746,456 B2 | 6/2004 | Xiao | |
| 6,746,472 B2 | 6/2004 | Frazier et al. | |
| 7,402,147 B1 * | 7/2008 | Allen | 602/20 |
| 2001/0049492 A1 | 12/2001 | Frazier et al. | |
| 2002/0002363 A1 | 1/2002 | Urakawa et al. | |
| 2002/0087176 A1 | 7/2002 | Greenhalgh | |
| 2003/0069629 A1 | 4/2003 | Jadhav et al. | |
| 2003/0208183 A1 | 11/2003 | Whalen et al. | |
| 2003/0229364 A1 | 12/2003 | Seiba | |
| 2004/0078047 A1 | 4/2004 | Nicholas et al. | |
| 2004/0087995 A1 * | 5/2004 | Copa et al. | 606/192 |
| 2005/0070938 A1 | 3/2005 | Copa et al. | |
| 2005/0131431 A1 * | 6/2005 | Copa et al. | 606/150 |

FOREIGN PATENT DOCUMENTS

| | | |
|---|---|---|
| WO | WO 96/07447 | 3/1996 |
| WO | WO99/16359 | 4/1999 |
| WO | WO 99/21490 | 5/1999 |
| WO | WO 99/21491 | 5/1999 |
| WO | WO 99/58081 | 11/1999 |
| WO | WO 04/000135 | 12/2003 |
| WO | WO 04/000136 | 12/2003 |
| WO | WO 04/000137 | 12/2003 |
| WO | WO 04/000138 | 12/2003 |
| WO | WO 2004/034913 | 4/2004 |

OTHER PUBLICATIONS

Acconcia et al., "Sutureless" Vesicourethral Anastomosis in Radical Retropubic Prostatectomy, The American Journal of Urology Review, vol. 1, No. 2, pp. 93-96 (Mar./Apr. 2003).

* cited by examiner

ANASTOMOSIS DEVICE CONFIGURATIONS AND METHODS

CROSS-REFERENCE TO RELATED APPLICATION

This application claims priority to U.S. Provisional application having Ser. No. 60/682,944, filed May 20, 2005, entitled "ANASTOMOSIS DEVICE CONFIGURATIONS", which application is incorporated herein by reference in its entirety.

TECHNICAL FIELD

The present invention relates to devices used for performing anastomosis and other related surgical procedures, including urethral procedures that involve reconnecting urethra and bladder tissues after a radical prostatectomy, vesicourethral anastomosis, and end-to-end urethral anastomosis.

BACKGROUND

Anastomosis procedures are required for connecting or re-connecting certain body tissues, such as in performing part of a surgical procedure. In particular, anastomosis procedures are used for joining one hollow vessel or structure to another hollow vessel or structure so that the interior portions of the vessel can fluidly communicate with each other. In one type of procedure, which may be referred to as an end-to-end anastomosis, severed tissues of a first vessel are coupled, usually by suturing or stapling, to severed tissues of a second vessel. The tissues may be part of a body lumen such as a blood vessel, intestinal or other digestive system tissue, or tissues relating to the urinary system. As one example, in a radical prostatectomy, a surgeon removes all or most of a patient's prostate. Because the urethra travels through the prostate immediately before reaching the bladder, the upper part of the urethra is also removed with the surgery. The procedure leaves a severed urethral stump and a severed bladder neck. To restore proper urinary functions, the bladder and the urethra must be reconnected, which can be a relatively difficult and complex procedure. These difficulties can occur as a result of the tendency of the urethral stump to retract into adjacent tissue after being severed and also due to the fact that the urethral stump is obscured by the pubic bone. These and other factors can make the area difficult to access by the surgeon, particularly for extending periods of time when performing the surgical procedure.

Conventionally, a surgeon may execute delicate suturing operations with tiny, fine needles to reconnect these or other anatomical bodies. However, installation of sutures with a needle to connect severed tissues can be a difficult and technique-sensitive task. Many factors can make the task difficult, including a very small amount of tissue to work with (e.g., at the urethral stump and at the bladder neck), and proximal sensitive tissues such as ureters at a bladder and a proximal nerve bundle and sphincter at a urethral stump. These factors result in complicated and delicate suturing procedures that, if not performed properly, could result in complications such as leakage, difficulty in healing or failure to heal, or specific conditions such as incontinence or impotence.

To reduce the risks involved in conventional suturing procedures, anastomosis devices have been developed that include a drainage feature and tissue approximating structures that allow for reconnection of tissues without using traditional sutures. These anastomosis devices advantageously use tissue approximating structures to reconnect severed tissues during anastomosis procedures, which can both reduce the risks during the surgical procedure and also provide a significant reduction in the amount of time required to perform certain anastomosis procedures. The tissue approximating structures can be activated by a number of different actuation mechanisms that the surgeon can use to extend and retract the tissue approximating structures relative to adjacent tissue structures, as desired. There is a need, however, to provide a variety of actuation mechanisms for anastomosis devices in different surgical situations, and also a desire to provide additional safety features and removal features for anastomosis devices.

SUMMARY

In one aspect of this invention, a surgical tool is provided which comprises an elongated body having a proximal end and a distal end, first and second sets of tissue approximating structures having deployed and retracted positions relative to the elongated body, an actuating mechanism extending from the proximal end of the elongated body for independently deploying and retracting each of the first and second sets of tissue approximating structures, a drainage lumen extending from a drainage aperture at the distal end of the elongated body to the proximal end, a main balloon adjacent to the distal end of the elongated body, and a strap connector extending from the elongated body that is connectable with a stabilization strap. In one embodiment, the strap connector comprises an aperture extending through a base portion of the strap connector. The tool may further comprise a stabilization strap having first and second opposite ends, wherein the first end is attachable to the second end for securing the strap around the leg of a patient and may further include an auxiliary strap attached to one face of the stabilization strap, wherein the auxiliary strap is removably attachable to the strap connector for attaching the stabilization strap to the elongated body.

In another aspect of the invention, a method of performing anastomosis is provided, the method comprising inserting a portion of an anastomosis device into a body lumen of a patient, wherein the anastomosis device comprises an elongated body having a proximal end and a distal end, first and second tissue approximating structures having deployed and retracted positions relative to the elongated body, and an actuating mechanism at the proximal end of the elongated body for independently deploying and retracting each of the first and second sets of tissue approximating structures. The method further comprises deploying the first and second tissue approximating structures into severed tissue of the patient by activating the actuating mechanism, maintaining the first and second tissue approximating structures within the severed tissue for a period of time, and using an extraction tool to disengage at least one of the first and second tissue approximating structures from the severed tissue. In one embodiment, the extraction tool comprises a tubular structure that has a diameter that is slightly larger than a diameter of the elongated body of the anastomosis device, and the method further comprises the step of sliding the extraction tool over the elongated body of the anastomosis device until it contacts one of the first and second tissue approximating structures and until the first and second tissue approximating structures are positioned within the extraction tool. The method further comprises removing the extraction tool and anastomosis device from the body lumen. In another embodiment, the extraction tool comprises a tubular structure that has a diameter that is slightly smaller than a diameter of a central drainage lumen positioned within elongated body of the anastomosis device. The extraction tool further comprises a cutting mechanism that is extendible from the tubular structure such that the method further includes severing the central drainage lumen with the cutting mechanism, contacting one of the first and second sets of tissue approximating structures with the cutting mechanism, and moving the contacted sets of tissue approximating structures laterally relative to the central drainage lumen.

BRIEF DESCRIPTION OF THE DRAWINGS

The present invention will be further explained with reference to the appended Figures, wherein like structure is referred to by like numerals throughout the several views, and wherein:

FIGS. 17 and 18 are top views of a tip configuration for use with anastomosis devices, wherein FIG. 17 shows a tip without a guide wire and FIG. 18 shows the tip of FIG. 17 with a guide wire positioned therein;

DETAILED DESCRIPTION

Figure 1:
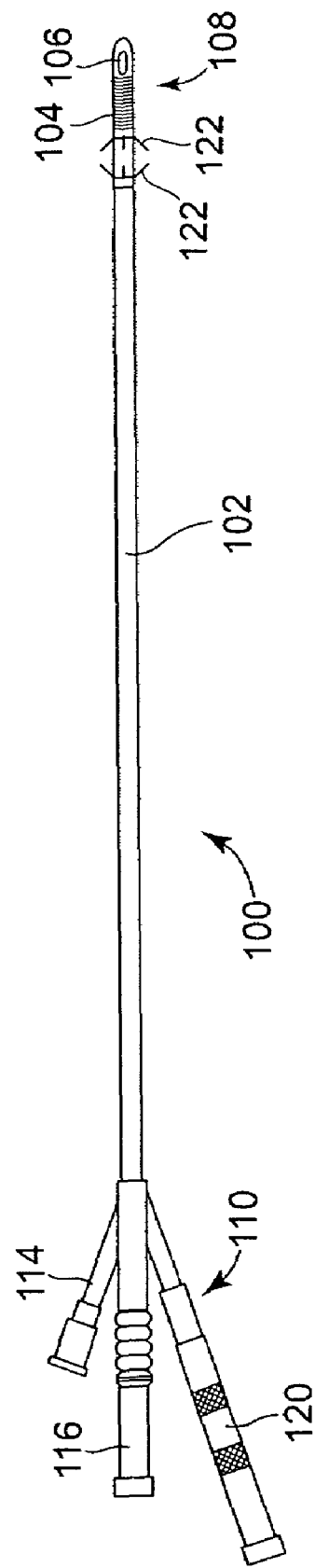
FIG. 1 is a top view of an exemplary anastomosis device of the type that can be used with the various configurations of the invention.

Referring now to the Figures, wherein the components are labeled with like numerals throughout the several Figures, and initially to FIG. 1, one preferred configuration of an exemplary embodiment of a modified-Foley-catheter-type anastomosis device that can used with the various configurations of the invention is illustrated. Device 100 includes a distal end 108, a catheter body 102, a balloon 104, and a drainage aperture 106. Tissue approximating structure can be located along the catheter body 102, for example, along catheter body 102 adjacent to balloon 104 near distal end 108. Tissue approximating structure of device 100 is shown as two sets of tines 122 (shown in an at least partially deployed position) but may alternatively include one or more additional sets of optionally opposing tines, a different type of elongate structure such as a probe or prod or needle, a balloon, or any other structure that may be used to place or hold severed tissue in contact with another opposing severed tissue for healing.

Device 100 further includes proximal end 110 opposite distal end 108. In the illustrated embodiment, proximal end 110 includes a port 114 that may connect to a lumen (not shown), such as an inflation lumen for balloon 104 or a drainage lumen from aperture 106. Another port, 116 can also be used with an inflation lumen or a drainage lumen. Device 100 further includes an actuating mechanism 120 for extending and retracting tines 122. The actuating mechanism can comprise, for example, a turnable knob or a lever (not shown), etc., that can be moved or rotated to extend or retract tines 122. Other variations of these features of the illustrated proximal end will be understood by those of skill, and may be used in combination with the features of the invention. In accordance with the invention, variations of several elements of an anastomosis device of the type generally described above relative to FIG. 1 are described as follows relative to the remaining Figures. However, it is understood that the features, configurations, and methods described below may be used with devices having a different configuration than that described relative to FIG. 1.

Figure 2:
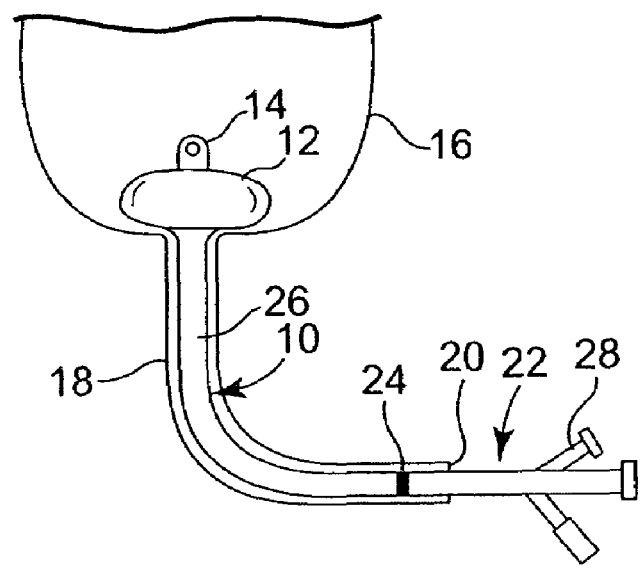
FIG. 2 is a schematic front view of an anastomosis device having quick-disconnection capabilities as viewed within an outline of a bladder and urethra of a patient.
Figure 3:
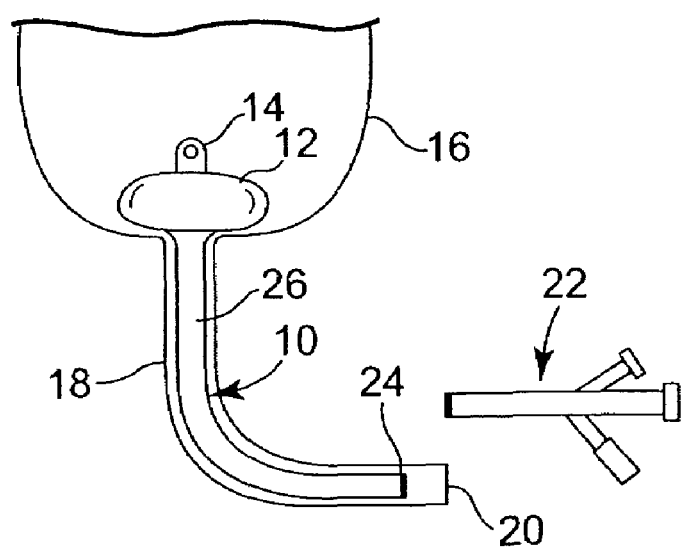
FIG. 3 is a schematic front view of the anastomosis device of FIG. 2, with the proximal portion of the device detached from the distal portion of the device.

FIGS. 2 and 3 illustrate an embodiment of an anastomosis device 10 having a balloon 12 that is shown as being at least partially inflated, and an adjacent drainage aperture 14. The balloon 12 is positioned within a patient's bladder 16 and is inflated sufficiently to maintain the device 10 generally in this position when subjected to normal external forces. An extension portion 26 extends from the balloon 12 through the patient's urethra 18 and through the urethral opening 20. The extension portion 26 of device 10 is preferably long enough that a proximal end 22 of device 10 can be positioned beyond the urethral opening 20. In this way, any ports (e.g., a port 28) of the anastomosis device 10 will be located outside the body when the device 10 is positioned within the patient. In a normal Foley-type catheter, if this device were purposely or inadvertently manipulated, such as with an external pulling force, the relatively large balloon 12 could be pulled into the relatively small opening of the urethra 18. This movement of the device can cause injury to the patient and prevent the device from performing its intended function. In cases where the device includes tissue approximating structures that are being used for connecting adjacent structures or tissues (e.g., urethral and bladder tissues), dislodging the anastomosis device can also cause the tissue approximating structures to disengage from the structures or tissues they are holding together, thereby potentially causing the patient additional trauma.

To prevent these undesirable consequences caused by external forces, device 10 is provided with quick-disconnect capabilities that allow the drainage aperture 14, balloon 12, and at least a part of the extension portion 26 to remain together in their original position within the patient through the use of a detachable connector 24. This connector 24 is positioned at some point along the length of extension portion 26 so that it can either be within the urethra 18 of the patient, as shown, or beyond the urethral opening 20 of the patient (i.e., outside the body). In either case, connector 24 is provided with sufficient attachment strength to maintain the integrity of the connection during normal movement of the patient. However, connector 24 is provided with a configuration that allows for disconnection of proximal end 22 of device 10 from the remainder of the device, such as when it is subjected to a certain, predetermined force. When such a disconnection takes place, the portion of device 10 that remains within the patient should allow for generally normal functioning of the device. That is, drainage of fluids from the bladder should still be able to occur, although the same controls, ports, and other features provided by proximal end 22 of the device would not be available. However, connector 24 preferably is configured to allow for reconnection of the same or a different end portion onto the portion of device 10 that remains in the patient's body. Thus, it may be desirable that extension portion 26 is sufficiently long to allow relatively easy access to the connector 24 after the device is positioned within the patient. A wide variety of configurations of such a quick-disconnect connectors are contemplated by the invention, which may be integral parts of the body itself and/or may include separate pieces or components that are added to the device to provide such a connection between components.

Figure 4:
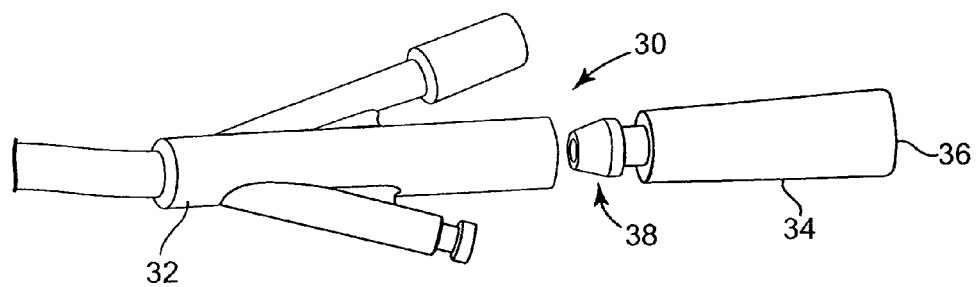
FIG. 4 is a perspective view of a portion of an anastomosis device of the type shown in FIGS. 2 and 3, illustrating one embodiment of a configuration for providing quick-disconnection capabilities.
Figure 5:
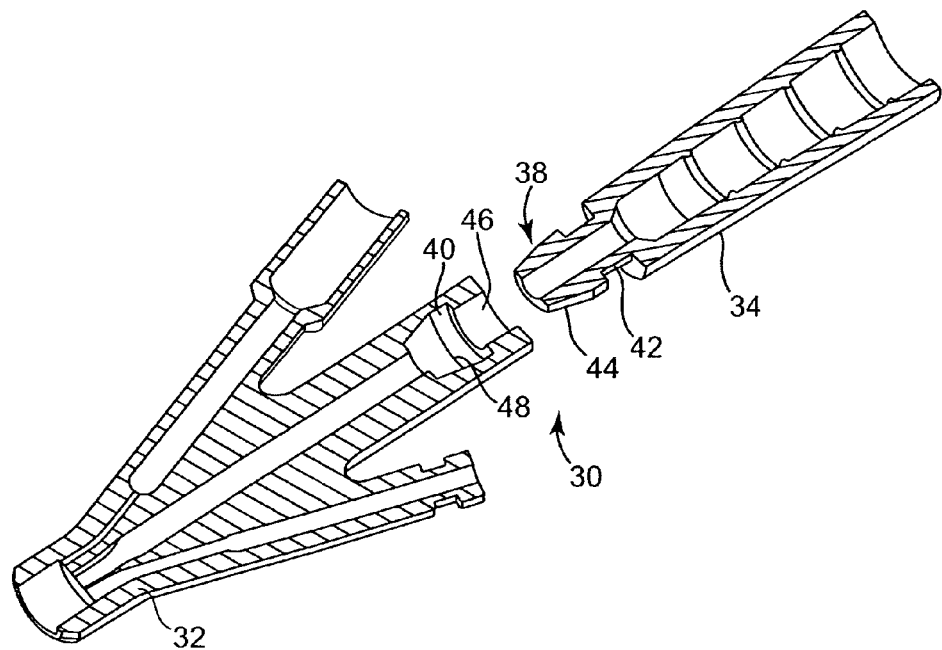
FIG. 5 is a cross-sectional perspective view of a portion of the anastomosis device of FIG. 4.

FIGS. 4 and 5 illustrate one embodiment of a two-piece catheter funnel 30 that will separate under certain loading conditions to prevent these loading conditions or forces from being transmitted to the tip of the device. For example, with regard to the device 10 of FIGS. 2 and 3, excessive external forces will be prevented from being transmitted to the drainage aperture 14 and its adjacent balloon 12, and any tissue approximation structures that may be provided on the device. In this embodiment, catheter funnel 30 includes a main funnel portion 32 and a drain adapter 34 having a drain adapter end 36. A drain (not shown) may attach to the device at this drain adapter end 36.

Drain adapter 34 includes a quick disconnect extension 38, which includes a neck 42 and an enlarged tip 44. A mating aperture 40 is provided at one end of main funnel portion 32 for engagement with extension 38 of drain adapter 34. In that regard, aperture 40 includes a neck 46 that corresponds with neck 42 of extension 38, and further includes an enlarged portion 48 that corresponds with enlarged tip 44 of extension 38. To connect drain adapter 34 to main funnel portion 32, extension 38 is pressed into main funnel portion 32 at neck 46 until it is engaged within mating aperture 40. Thus, one or both of enlarged tip 44 of extension 38 and neck 46 of aperture 40 will be at least slightly deformable to allow the larger-sized tip 44 to pass through the smaller-sized opening of neck 46. In addition, enlarged tip 44 may be provided with a taper, as shown, to provide for easier passage into the aperture 40. This connection between main funnel 32 and drain adapter 34 is configured to be generally robust under normal movements and forces provided by patient movements. However, the sizes, shapes, materials, and other properties of these components are selected so that funnel 32 and adapter 34 will disconnect from each other when a predetermined external force is received by device 30. This predetermined external force is selected to be at least slightly less than the force required to dislodge or otherwise displace the device from the patient to avoid or minimize patient trauma.

Figure 6:
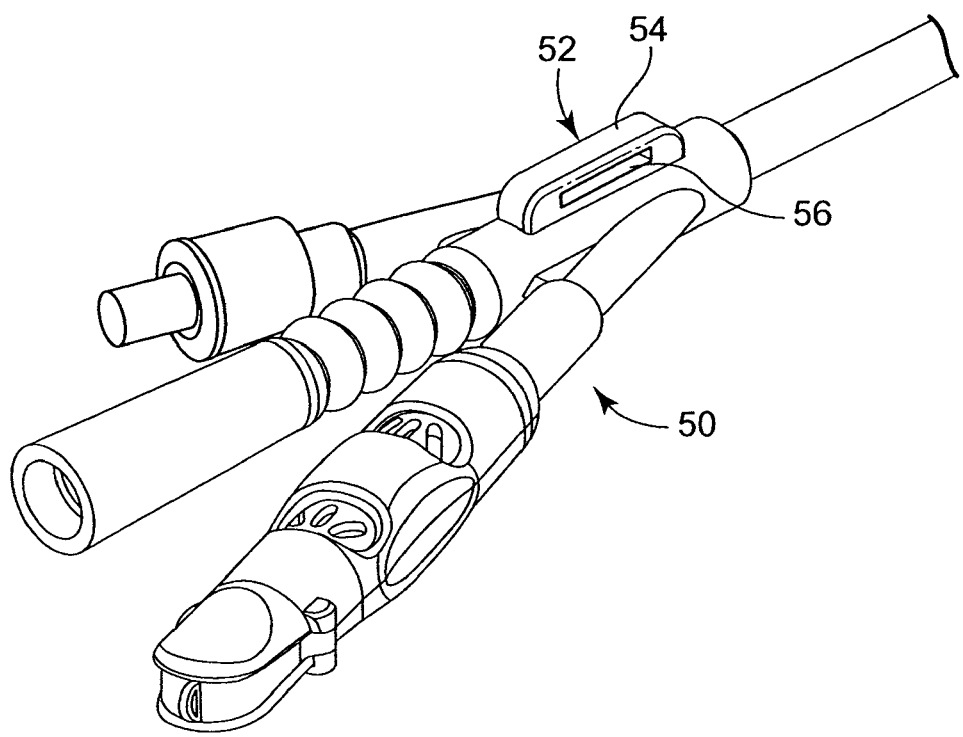
FIG. 6 is a perspective view of an end portion of an anastomosis device, including a body strap attachment feature.
Figure 7:
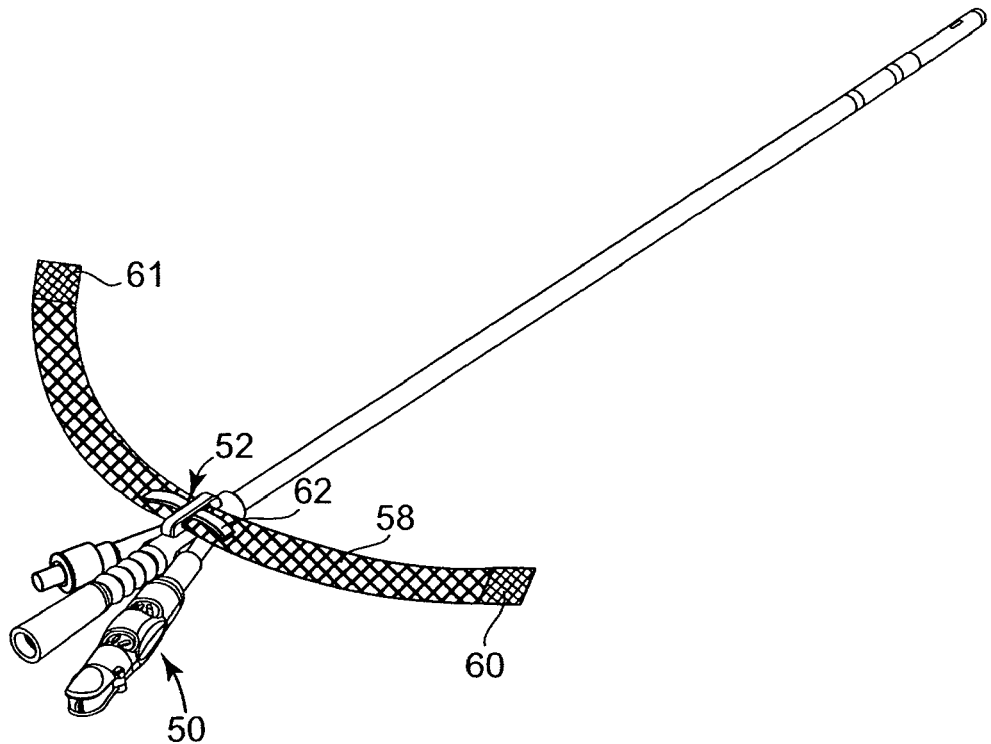
FIG. 7 is a perspective view of an anastomosis device that includes the body strap attachment feature of FIG. 6, and further including a body strap engaged with the body strap attachment feature.

FIGS. 6 and 7 illustrate an integrated feature on a catheter funnel that mates with a standard or custom catheter leg strap or Foley catheter holder to create additional protection from external forces on the catheter that exceed a certain level. That is, a leg strap is provided to hold the device in place relative to a patient's leg when the device is installed in a patient's body, thereby absorbing outside impacts, jerking motions, and the like, and minimizing the chances of undesirable forces being transmitted to the device. Such a leg strap may be used in addition to or instead of the quick-disconnect features described above relative to FIGS. 4 and 5.

In particular, FIG. 6 shows one embodiment of a feature that can be used to accept or connect with a leg strap, which is illustrated with an end portion 50 of an anastomosis device or other catheter-type device. End portion 50 includes a leg strap attachment device 52 extending from the outer surface of its main body. Device 52 includes a body 54 having a slot 56 extending laterally through its thickness. Slot 56 is provided with a size and shape to be able to accept a strap or connector, yet is preferably provided to be as small as possible to prevent the device to which it is attached from being overly cumbersome. The device 52 may be positioned at any point along the length of end portion 50 that corresponds with an area of the device that will be positioned outside the body of the patient when installed therein.

Device 52 is further illustrated in FIG. 7 with a stabilization or leg strap 58 that is sufficiently long to be able to encircle the leg of a patient. Leg strap 58 further includes an auxiliary strap 62 that extends through the slot 56 of device 52. Auxiliary strap 62 has opposite ends that are attached to the body of strap 58, either by one or more permanent connections or by one or more temporary connections (e.g., a hook-and-loop type of connection) to connect the strap 58 to the device 52. Alternatively, leg strap 58 can be inserted through the slot 56 without the use of an auxiliary strap 62. In any case, a wide variety of configurations are contemplated by the present invention for attaching a leg strap to the end portion of a device, which may include adhering or otherwise bonding an auxiliary strap to the leg strap, providing leg strap attachment devices with one or more slots, clamps, or other configurations for accepting a leg strap, or the like.

The leg strap itself is preferably made of a relatively flexible and strong material that can encircle the leg of a patient, and may be provided as a single elastic band, for example, or may have two ends 60, 61 that are attachable to each other after the strap is positioned relative to the patient's leg. For example, end 60 may include a loop fastener and end 61 may include a mating hook fastener so that the ends 60, 61 can be connected to each other by pressing them together after the strap 58 encircles the leg of a patient. The configuration of the leg strap should further accommodate removal from the patient when desired, and further can include end portion attachments that can be reused multiple times, such as for repositioning or adjusting the leg strap.

Figure 8:
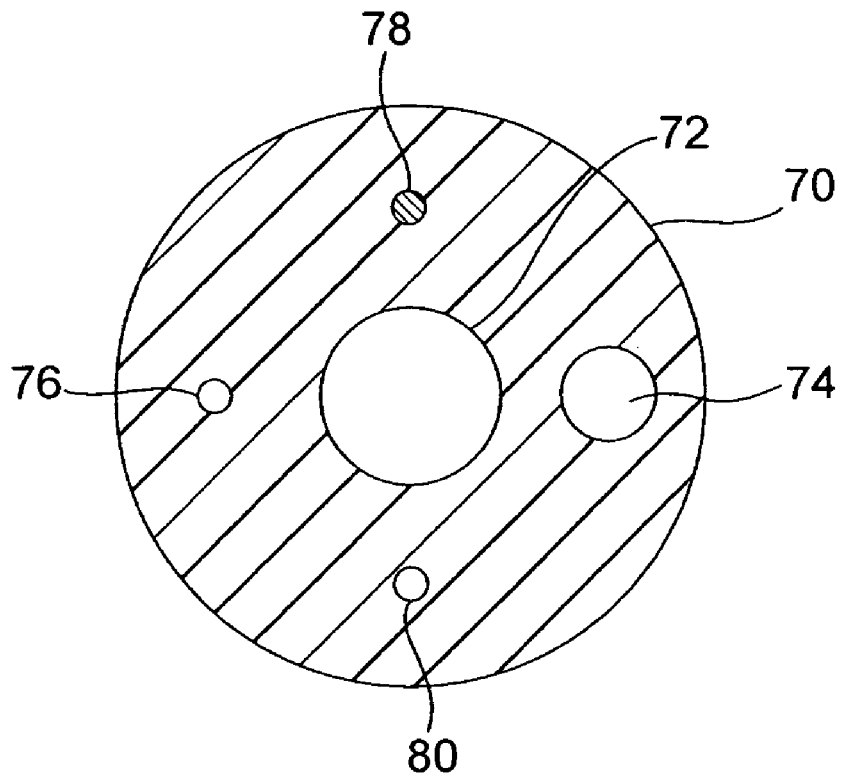
FIG. 8 is a cross-sectional end view of one embodiment of a catheter construction of the present invention.
Figure 9:
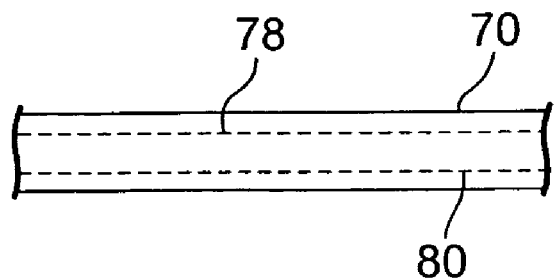
FIG. 9 is a side view of a portion of the catheter illustrated in FIG. 8.

Referring now to another aspect of catheter constructions, it is known to co-extrude a single wire, cable, or monofilament with the silicone or other material from which the catheter itself is constructed. Such a wire is often provided to prevent or limit stretching of the catheter shaft when in use, and is offset from the center drainage lumen of the catheter. However, in some cases, as the material from which the catheter is made hardens, it can grab or attach to the wire in that part of the catheter body in such a way that it does not shrink in the same way as the material on the opposite side of the catheter. This uneven shrinking of the material can result in at least a slight bend or curvature along the catheter length, which may be undesirable for some applications. FIG. 8 illustrates one manner of making a catheter using an extrusion process in order to provide a straighter catheter shaft. In particular, an end view of a portion of a catheter body 70 is illustrated, which includes a generally central drainage lumen 72, an actuation wire lumen 74, an air lumen 76 (e.g., for balloon inflation and deflation), and a first co-extruded wire, cable or monofilament 78. This catheter construction of the invention further includes adding a second co-extruded wire 80 spaced on a generally opposite side of the drainage lumen 72 from the first co-extruded wire 78, as is also illustrated in FIG. 9. However, second wire 80 may be positioned in any location in the catheter body 70 that provides a more even cooling of the structure, and therefore provides for a more straight extrusion.

In accordance with the invention, second wire 80 may be coated with a non-stick material, such as a material commercially available from DuPont of Wilmington, Del., under the trade name "TEFLON". In this way, the second wire 80 can be removed from the catheter after the catheter body has hardened. Such wire removal is optional, but may be desirable to maintain a certain flexibility of the catheter for use during a surgical procedure. That is, second wire 80 can either be a permanent part of the catheter body construction, or may be entirely or partly removable after it has served its purpose of keeping the catheter body straight during and after the extrusion process. In certain configurations of a catheter body, it may further be desirable to add even more wires during the co-extrusion process, such as may be desirable to provide certain properties to the catheter. These wires may be made to either be removable or permanent in the catheter construction.

FIGS. 10-15 illustrate methods and devices for creating linear movement in order to activate a mechanism from a remote source. More particularly, these Figures show and describe various methods and devices that will activate linear motion in an anastomosis device so that proximal, internal approximation structures may be actuated by a distal, external control mechanism. The approximation structures referred to herein generally refer to bladder tines and urethral tines, where any of the activation devices can be used to equally refer to either or both of these types of tines. However, if an anastomosis device is used to connect different types of tissues, each set of tines will be specifically structured for connection to that tissue.

Figure 10:
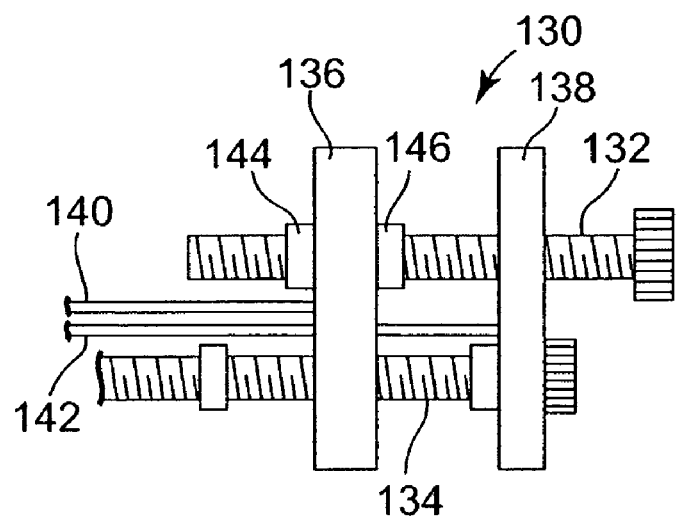
FIG. 10 is a top view of a configuration for controlling actuation wires for approximating structures of an anastomosis device, which includes a pair of screws.

Referring now to FIG. 10, one embodiment of an activation device 130 is illustrated. Device 130 can be located, for example, generally at the proximal end of an anastomosis device, such as at the proximal end 110 of the device 100 of FIG. 1. Device 130 is a screw drive for moving the actuation wires linearly, and generally comprises a first screw 132, a second screw 134, a first block 136, a second block 138, a first actuation wire 140, and a second actuation wire 142. First and second actuation wires 140, 142 are attached to separate approximation structures (not shown) that are located remotely from the activation device 130. First screw 132 is locked to first block 136 with a pair of bolts 144, 146, positioned on opposite sides of block 136, although it is possible that the first screw 132 is fixed to first block 136 using a different type of connection configuration. First screw 132 is threaded along its length and second block 138 includes a threaded opening (not visible) for engagement with the threads of first screw 132. Second block 138 further includes a non-threaded hole (not visible) through which the second screw 134 extends, and first block 136 includes a threaded hole (not visible) for engagement with the threads of second screw 134. First actuation wire 140 is attached to first block 136, and second actuation wire 142 extends through a hole in first block 136 and is attached to second block 138.

In operation, rotation of first screw 132 will move first block 136 laterally relative to the length of screw 132, thereby moving actuation wire 140 in a direction that is generally parallel to the length of screw 132. Meanwhile, second block 138 will remain stationary. Similarly, rotation of second screw 134 will move second block 138 laterally relative to the length of screw 134, thereby moving actuation wire 142, which is attached to second block 138, in a direction that is generally parallel to the length of second screw 134. Screws 132, 134 can be rotated through the use of either a manual driver or an automatic driver to move the actuation wires 140, 142, respectively, thereby retracting or withdrawing approximation structures remotely located from the device 130. Thus, two sets of approximation structures (e.g., bladder tines and urethral tines) can be deployed and retracted independently of one another.

Figure 11:
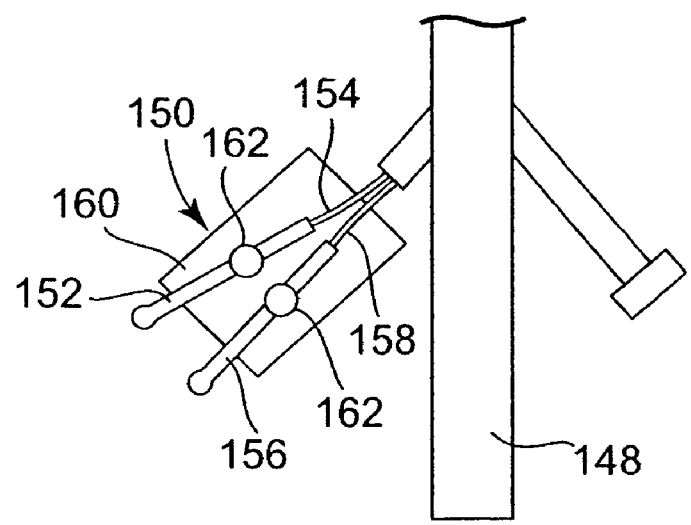
FIGS. 11-13 are top views of additional configurations for controlling actuation wires for approximating structures of an anastomosis device.
Figure 12:
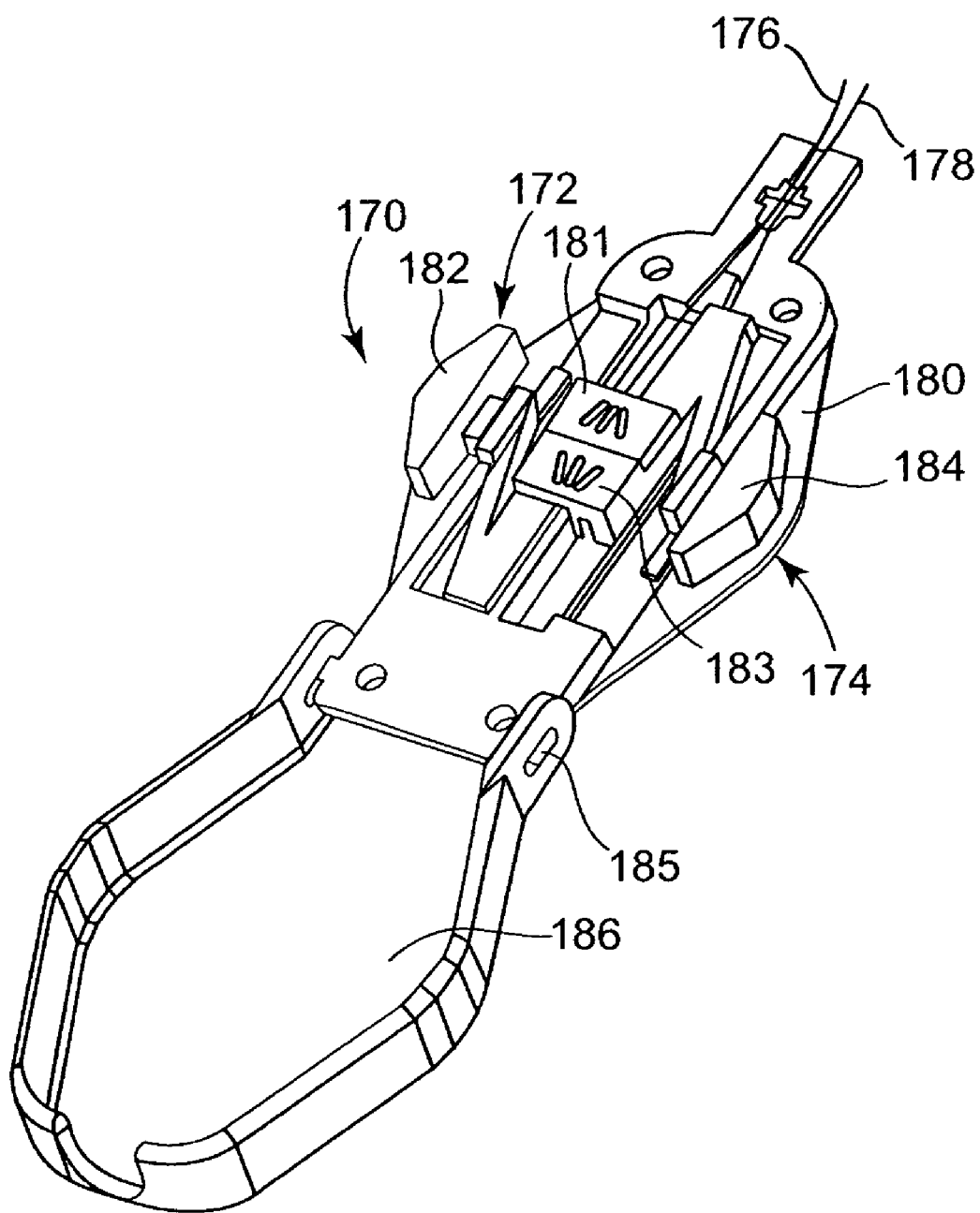
Figure 13:
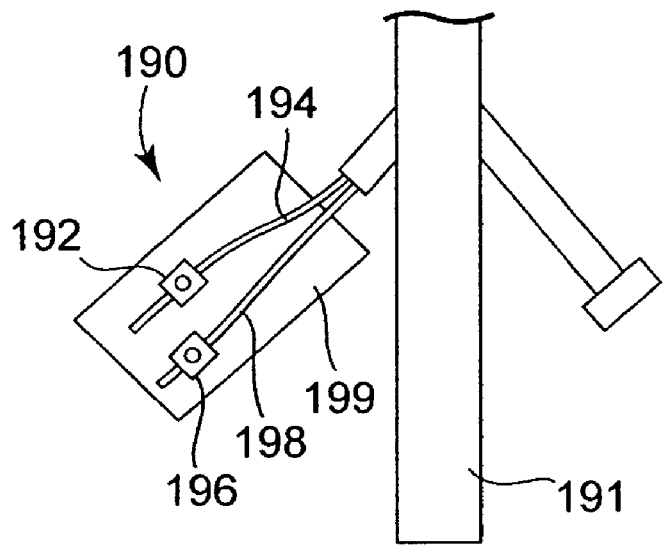

FIGS. 11-13 illustrate embodiments of activation devices that can be located generally at the proximal end of an anastomosis device, such as at the proximal end 110 of the device 100 of FIG. 1. All of these devices include the use of advancement structures or devices that "pull" an actuation wire to deploy one approximation structure (e.g., bladder tines) and "push" an actuation wire to deploy another approximation structure (e.g., urethral tines). In order to retract these approximation structures, the opposite action is performed with the advancement structures or devices (e.g., pulling instead of pushing, and vice versa).

In particular, FIG. 11 illustrates a catheter body 148 from which an activation device 150 extends. Device 150 generally includes a first arm 152 connected to a first actuation wire 154, and a second arm 156 connected to a second actuation wire 158. Both arms 152 and 156 are slideably mounted to a plate 160, which may include channels in which arms 152, 156 are positioned. Arms 152, 156 are independently moveable to push or pull their respective actuation wires, which in turn will deploy or retract the approximation structures that are remotely located relative to the device 150. Device 150 can further include one or more locking members 162 for maintaining arms 152, 156 in place once the actuation wires 154, 158 have been moved or slid into their desired positions. In this embodiment, locking members 162 are in the form of buttons that can be pressed downwardly to put pressure on their respective arms 152, 156 within the channels in the plate 160 and lock them in place. The locking members 162 may then be at least partially released when it is desired to allow arms 152, 156 to be repositioned. This sequence can be repeated multiple times during the process of deploying and retracting approximation structures, if needed or desired.

FIG. 12 illustrates an activation device 170 that generally includes a first mechanism 172 connected to a first actuation wire 176, and a second mechanism 174 connected to a second actuation wire 178. For clarity of illustration, mechanism 172 is shown as being shaded in the figure, and mechanism 174 is not shaded. Both mechanisms 172 and 174 are slideably mounted within a recess of a casing 180, which may include channels in which portions of mechanisms 172, 174 are positioned, or may include other guiding devices. Mechanism 172 includes a base 181 connected to a release button 182 via at least one connector arm, and mechanism 174 includes a base 183 connected to a release button 184 via at least one connector arm. To operate the mechanism 172, release button 182 is squeezed toward the center of the casing 180 and toward base portion 181, and then the mechanism 172 can be moved along the length of the casing 180 by a desired distance. Similarly, to operate the mechanism 174, release button 184 is squeezed toward the center of casing 180 and toward base portion 183, and then the mechanism 174 can be moved along the length of the casing 180 by a desired distance. Mechanisms 172, 174 are independently moveable to push or pull their respective actuation wires, which in turn will deploy or retract the approximation structures that are remotely located relative to the device 170.

Device 170 can further include a cover 186 that is connected to casing 180 via a hinge 185. Cover 186 can be used for maintaining mechanisms 172, 174 in place once the actuation wires 176, 178 have been moved or slid into their desired positions. Cover 186 may further be used to verify that the mechanisms 172, 174 are in a certain position, since the cover 186 will interfere with release buttons 182, 184 in certain arrangements of the components. In this embodiment, cover 186 can only close when the buttons of the mechanisms 172, 174 are in a certain position, such as when the actuation wires are deployed. In this way, a health provider and the patient can be sure that the actuation wires are properly positioned and that they will stay in that position once cover 186 is closed.

Another activation device 190 is illustrated in FIG. 13, which is similar in operation to the device 150 of FIG. 11. Activation device 190 extends from a catheter body 191, and generally includes a first button 192 connected to a first actuation wire 194, and a second button 196 connected to a second actuation wire 198. Both buttons 192 and 196 are slideably mounted to a plate 199, which may include channels in which buttons 192, 196 and/or actuation wires 194, 198 are positioned. Buttons 192, 196 are independently moveable to push or pull their respective actuation wires, which in turn will deploy or retract the approximation structures that are remotely located relative to the device 190. Device 190 can further include one or more locking members (not shown) for maintaining arms 192, 196 in place once the actuation wires 194, 198 have been moved or slid into their desired positions.

Figure 14:
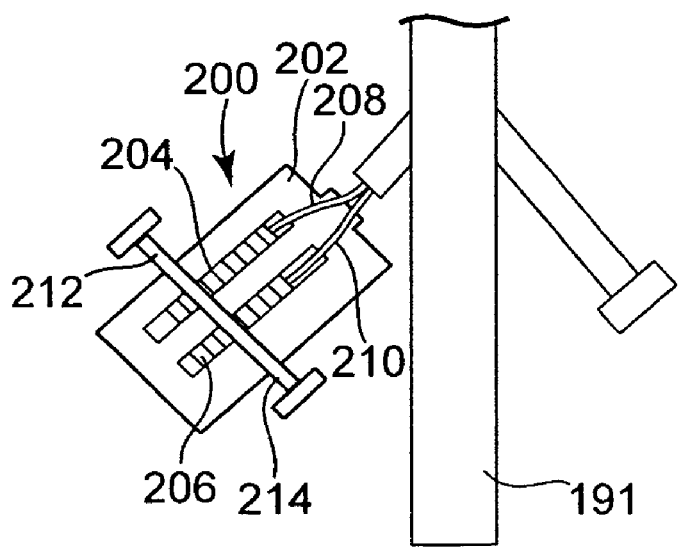
FIGS. 14 and 15 are top views of a configuration for activating the actuation wires that control approximating structures of an anastomosis device, which includes a "rack and pinion" type of activation.
Figure 15:
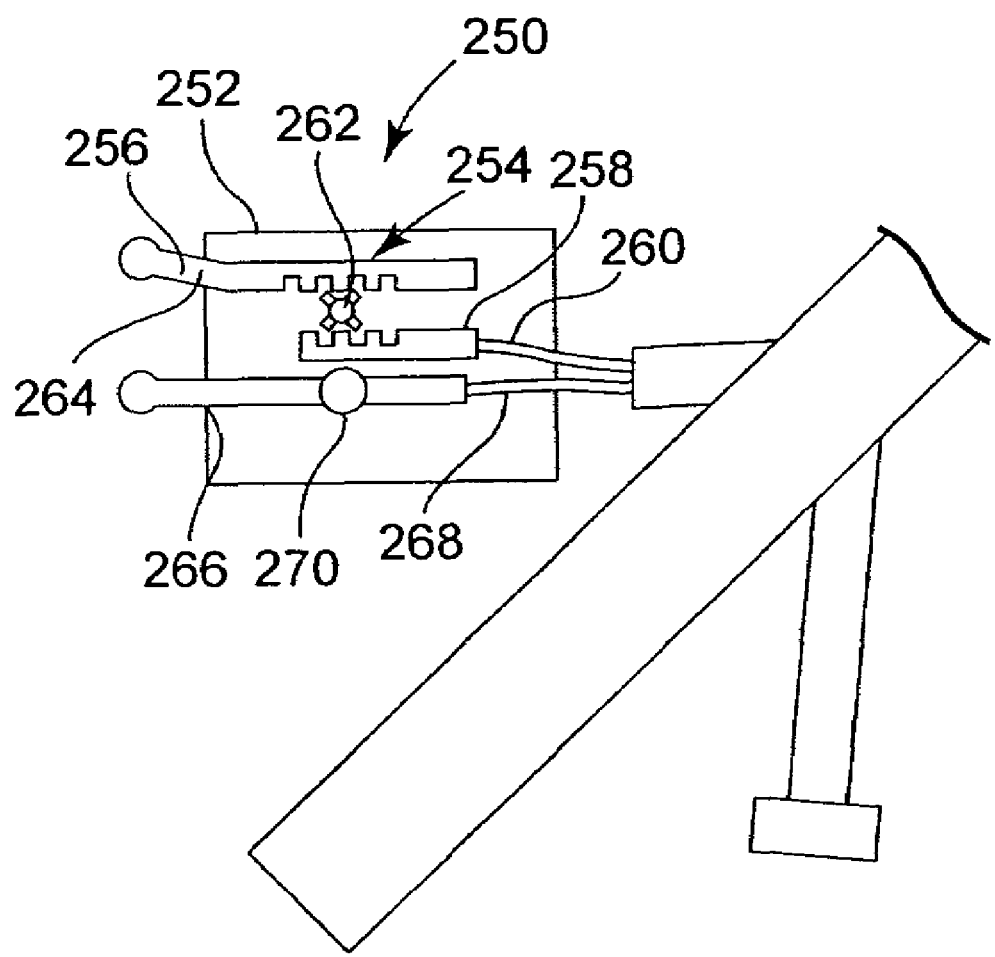

FIGS. 14 and 15 illustrate additional alternative embodiments of activation devices that would be located generally at the proximal end of an anastomosis device, such as at the proximal end 110 of the device 100 of FIG. 1. These devices are somewhat similar to those of FIGS. 11-13 in that they also use the motions of pushing and pulling actuation wires to deploy and retract approximation structures. However, these devices utilize a rack and pinion type of arrangement of gears that effectively push and pull the advancement arms. In particular, FIG. 14 shows an activation device 200 that includes a base plate 202 on which a first rack 204 and a second rack 206 are mounted. First rack 202 is connected to a first actuation wire 208 and second rack 206 is connected to a second actuation wire 210. Device 200 further includes a first wheel gear 212 and a second wheel gear 214 that mesh with the teeth of first and second racks 202, 206, respectively. Rotation of the first wheel gear 212 thereby moves the rack 202 back and forth due to the engagement of the wheel gear 212 with the rack 202, which causes a corresponding movement of the first actuation wire 208. Similarly, rotation of the second wheel gear 214 moves the second rack 206 back and forth due to the engagement of the wheel gear 214 with the rack 206, which causes a corresponding movement of the second actuation wire 210. Because two wheel gears 212, 214 are used in this embodiment, the actuation wires can be operated independently for separate deployment and retraction of approximation structures.

FIG. 15 illustrates an activation device 250 that again utilizes the concept of a rack and pinion configuration for controlling the movement of one of the actuation wires. Activation device 250 includes a base plate 252 on which a rack and pinion structure 254 is mounted. Structure 254 includes a first rack 256, a second rack 258 that is connected to a first actuation wire 260, and a gear 262 positioned to engage with the gears of both racks 256, 258. Rack 256 further includes an arm 264 that can be grasped for pulling or pushing to move the actuation wire 260. In particular, pulling the arm 264 will cause the rack 256 to turn the gear 262 in a counterclockwise direction, which in turn will move the rack 258 toward the actuation wire 260, thereby "pushing" the actuation wire 260. Activation device 250 further includes an arm 266 connected to a second actuation wire 268. Arm 266 may be slideably mounted to plate 252, which may include a channel in which arm 266 is positioned. Arm 266 may be lockable with a locking mechanism 270. It is understood, however, that the device 250 may instead include a different configuration for movement of wire 268 than the arm 266, such as another rack and gear configuration similar to that of structure 254. Thus, the actuation wires 260, 268 are independently moveable to push or pull their respective actuation wires, which in turn will deploy or retract the approximation structures that are remotely located relative to the device 250.

A number of other concepts are contemplated to create linear movement in order to activate a mechanism from a remote source. As described above relative to FIGS. 11-15, the following concepts for various methods and devices are useful to activate linear motion in an anastomosis device so that the proximal, internal approximation structures may be actuated by a distal, external control mechanism. One such concept of the invention relates to a detachable actuation mechanism that can be detached from the main body of the device after actuation has been achieved. The benefit of this design would be that individuals (e.g., patients) could not manipulate the device once placed. To remove the device, the actuation mechanism could be reattached to the main body.

Another embodiment of the invention relates to incorporation of an inflation valve into the actuation mechanism. In particular, a balloon inflation valve can be incorporated into the actuation mechanism such that a preferential sequencing could be directed. Specifically, the preferred sequencing would be to inflate the bladder balloon, actuate the bladder tines, and then actuate the urethral tines. After deploying the tines, the balloon inflation valve would be "locked out" until the tines have been retracted. This design feature may prevent mistaken removal of the device prior to complete tine retraction.

Other concepts relate to the use of hydraulic and/or pneumatic activation of approximation structures by means of manipulating fluid pressure and/or positioning within a system, and the use of magnetic and/or electromotive activation of approximation structures by applying magnetic or electric current.

In a device having multiple sets of approximating structures, a separate actuation wire can be provided in the device for each set of tissue approximating structures to allow for independent extension and retraction of the tissue approximating structures, as desired. That is, individual components of a specific approximation structure can be activated independently of the other components of the same approximation structure. In accordance with the invention, both of the actuation wires can be connected within a single actuation mechanism that can be manipulated to provide the desired movement of the tissue approximating structures.

Figure 16:
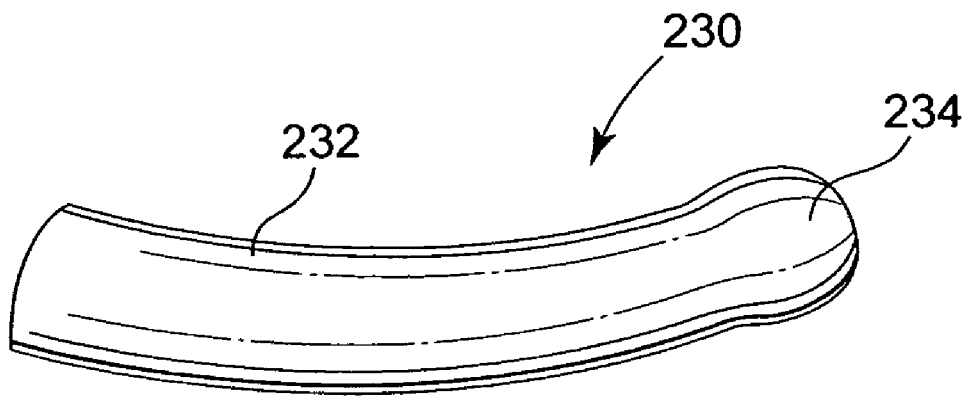
FIG. 16 is a top view of a tip configuration for use with anastomosis devices.
Figures 17, 18:
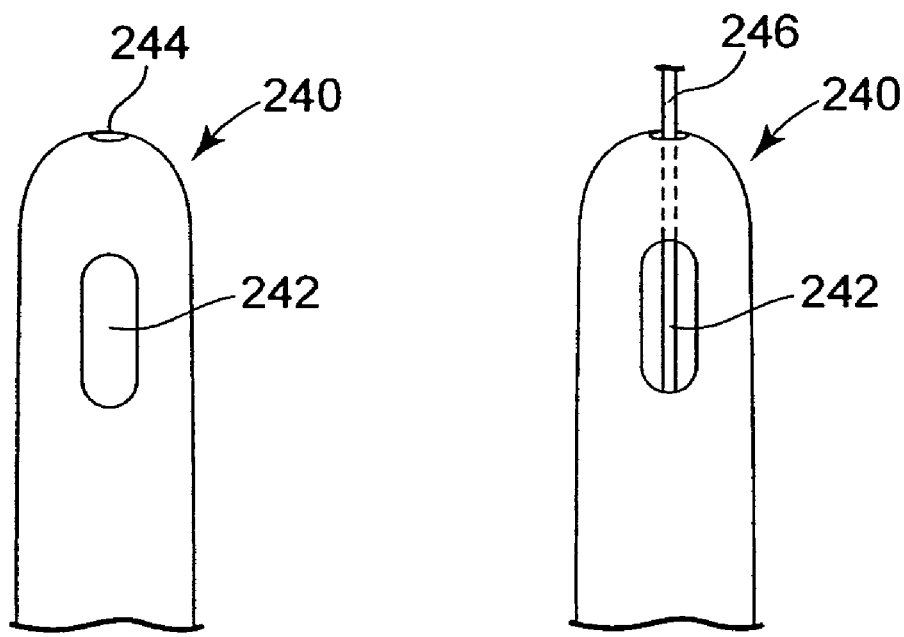

The anastomosis devices of the invention may be provided with various tip configurations relative to the delivery and/or exchange of the device, which may be used with the type of device illustrated in FIG. 1, for example. For one example, the tip can be curved into a configuration known as a coude configuration to generally match the curvature of the patient's anatomy and ease the delivery of the device. One embodiment of a coude tip is illustrated in FIG. 16. As shown, a tip 230 comprises a curved portion 232 that extends from a relatively spherical end portion 234. This configuration provides for easier insertion of the device with less potential trauma to the patient. For another embodiment of a tip, a device may be provided with a council tip to ease in the exchange of the device in the event that an original device needs to be removed, such as is illustrated in FIGS. 17 and 18. As shown, a tip 240 includes a drainage aperture 242 and a hole 244 at its end to accommodate a guide wire 246, which is illustrated in FIG. 18. The use of such a guide wire can aid in the maneuverability of the device to difficult areas of the patient's anatomy.

Other features may be provided for the anastomosis devices described herein, or for other anastomosis devices. One such feature involves providing a lubricious coating to ease the delivery and/or exchange of the device. The coating can be covalently or non-covalently bonded. The device can be provided in a pre-coated form, or may instead be coated at the time of usage. Another feature is to provide an anastomosis device with an antimicrobial coating on a portion or on the entire device. Such a coating can reduce the likelihood of a urinary tract infection. Another feature is to deliver therapeutic agents via the anastomosis device. Methods of achieving this function can include utilizing needles as approximation structures, adding an additional lumen to administrate drug delivery while the device is placed, or incorporating a drug release mechanism on portions of the device.

Figure 19:
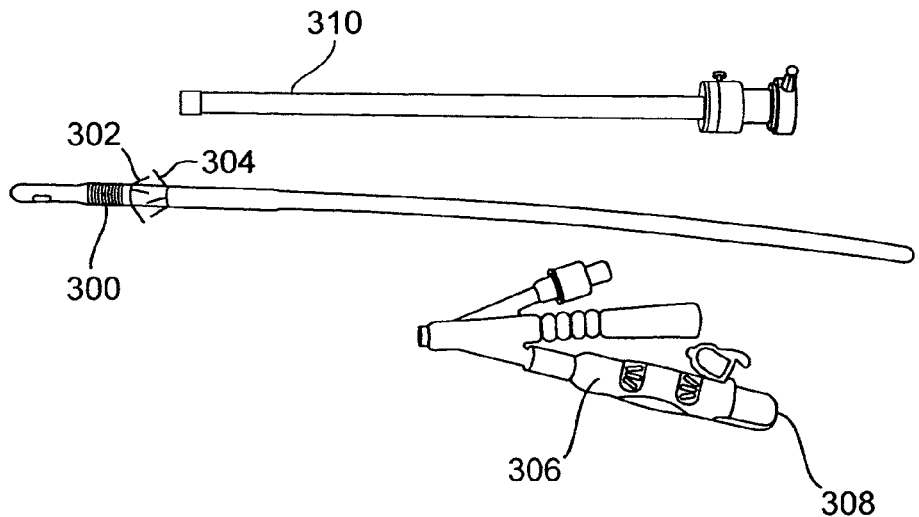
FIGS. 19-23 illustrate top views of a device used for disengaging tissue approximating structures of an anastomosis device from the tissue they are penetrating, including a sequential representation of steps to accomplish tissue disengagement and removal of the anastomosis device.

The concepts of FIGS. 19-31 describe methods and devices that can be used in conjunction with an anastomosis device in the event that the urethral or bladder tines do not fully retract to disengage from the tissue of the patient, or in a case where the actuation mechanism becomes disconnected when the device is in the patient's body. In a first method, FIGS. 19-23 illustrate the steps of removing the anastomosis device with a resectoscope sheath for cases where the tines do not fully retract or become disconnected from their control mechanism. In particular, FIG. 19 shows a catheter tube 300 having two sets of deployed tines 302, 304. A representative proximal end portion 306 having an actuation mechanism 308 is also shown, as an illustration of the disconnection of the tines from an actuation mechanism. Notably, the balloon of catheter tube 300 would likely deflate, as shown, upon disconnection of the proximal end portion 306. In addition, a representative resectoscope 310 that will be used to change the configuration of the deployed tines is shown, which has a diameter that is at least slightly larger than the outer diameter of catheter tube 300.

Figure 20:
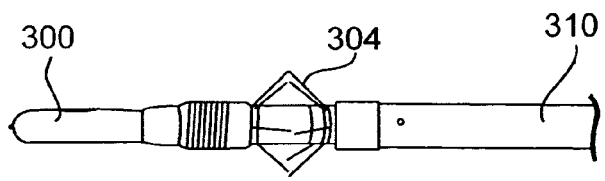
Figure 21:
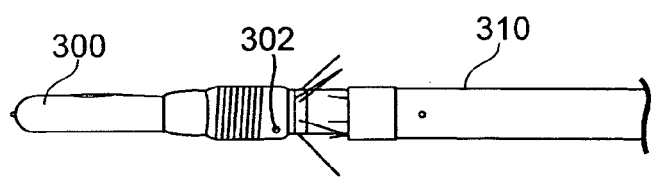
Figure 22:
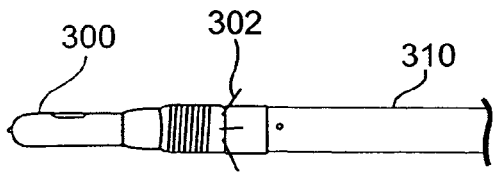
Figure 23:
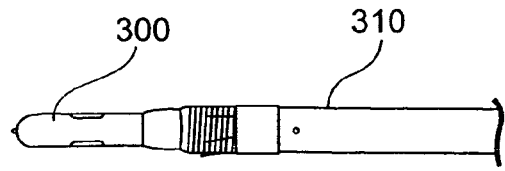

Resectoscope 310 is slid onto the end of tube 300 opposite the tip of the device, until it contacts the tines 304 (e.g., the urethral tines), as shown in FIG. 20. The catheter tube 300 is then pulled toward resectoscope 310 while maintaining the position of resectoscope 310 to minimize trauma to the surrounding urethral tissue, as shown in FIG. 21. Tines 304 will then be positioned within the interior area of resectoscope 310. The catheter tube 300 is then pulled further toward resectoscope 310 until it contacts the tines 302 (e.g., the bladder tines), as illustrated in FIG. 22. Catheter tube 300 is pulled even further toward resectoscope 310 until tines 302 are also enclosed within the interior area of resectoscope 310, as shown in FIG. 23. At this point, the tines 302, 304 are no longer engaged with any tissue, and in fact are partially or completely enclosed within resectoscope 310. The resectoscope/catheter tube assembly can then be removed from the patient without causing trauma to the surrounding tissue.

Figure 24:
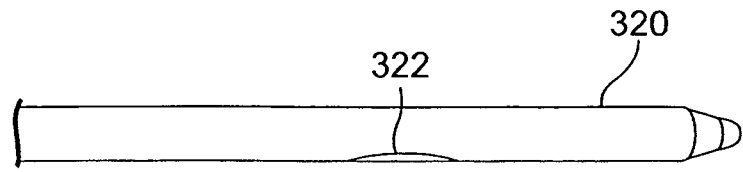
FIGS. 24-31 illustrate top views of a revision tool used for disengaging tissue approximating structures of an anastomosis device from the tissue they are penetrating, including a sequential representation of the steps to accomplish tissue disengagement and removal of the anastomosis device.
Figure 25:
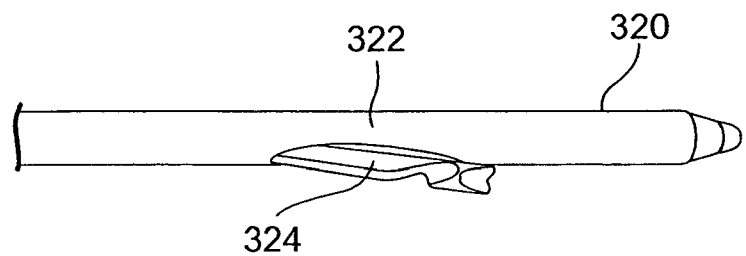
Figure 26:
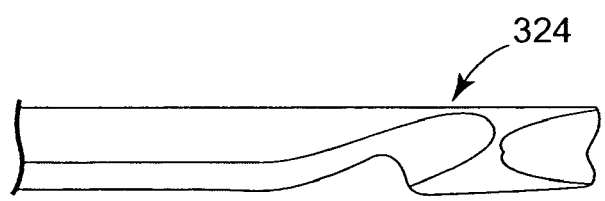
Figure 27:
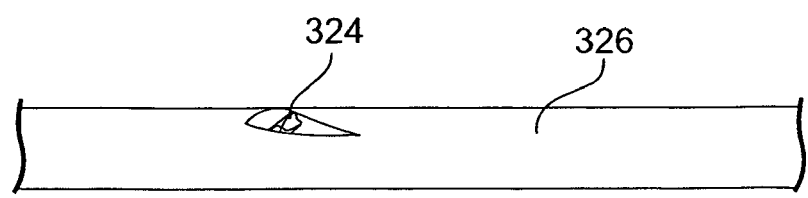

FIGS. 24-27 illustrate the steps of another method of removing the removing the anastomosis device with a custom revision tool for cases where the tines do not fully retract or become disconnected. These steps can be performed blindly, or may be performed using visualization techniques, such as fluoroscopy, ultrasound, and the like. With reference to FIG. 24, a revision tool 320 is shown, which is chosen to be a size that will fit within the central drainage lumen of a catheter. That is, the revision tool 320 consists of an outer sheath that has an outside diameter that is smaller than the inside dimension of the anastomosis device. The tip of the outer sheath is blunt and has a side hole 322 a short distance from the tip. Side hole 322 has an angled feature that begins at the edge of the hole closest to the tip and continues to the opposite side of the sheath. Revision tool 320 further includes an inner tube with a cutting mechanism 324, which is illustrated in FIGS. 25 and 26. Cutting mechanism 324 is also visible in FIG. 27, which shows cutting mechanism 324 penetrating the wall of a flexible core tubing 326 in which the revision tool 320 is inserted. When cutting is advanced within the outer sheath, it follows the angled feature of the outer sheath and is deflected away from the axis of the revision tool. The tool is used to cut through the flexible core tubing 326 of the anastomosis device from within the device. The tool can further be used to attach to the individual hubs in order to retract the tines, as described in further detail below.

Figure 28:
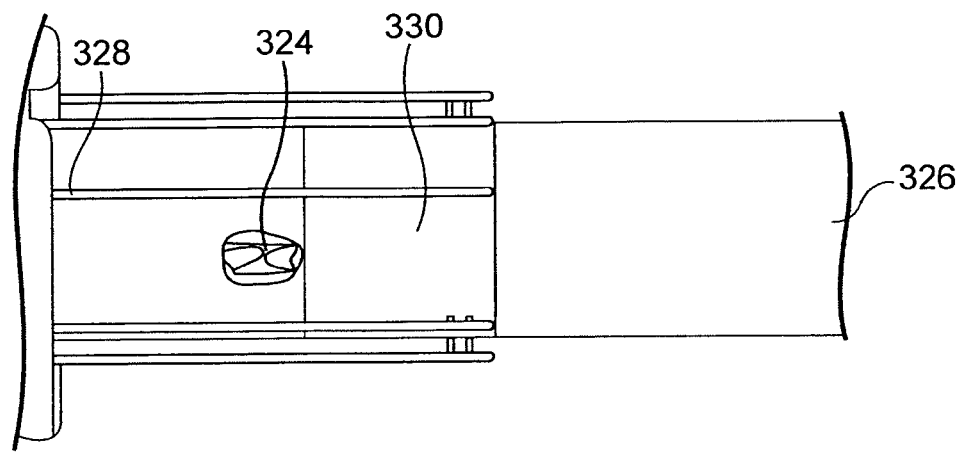
Figure 29:
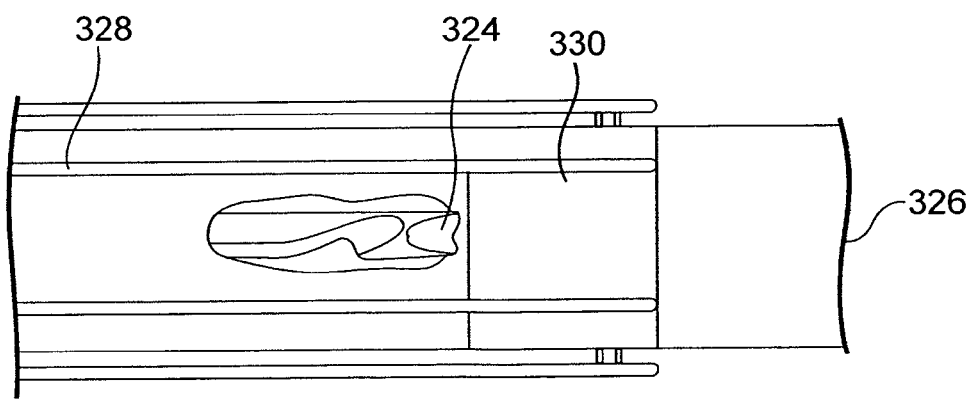

FIGS. 28-29 illustrate a method for retracting bladder tines 328, which are arranged about a hub 330. In particular, a revision tool is inserted within tube 326, and when the tool is in the correct position, cutting mechanism 324 is used to penetrate tube 326 at the desired place relative to the tines 328. The revision tool is then moved relative to tube 326 so that cutting mechanism 324 will push the hub 330 laterally, thereby retracting the bladder tines.

Figure 30:
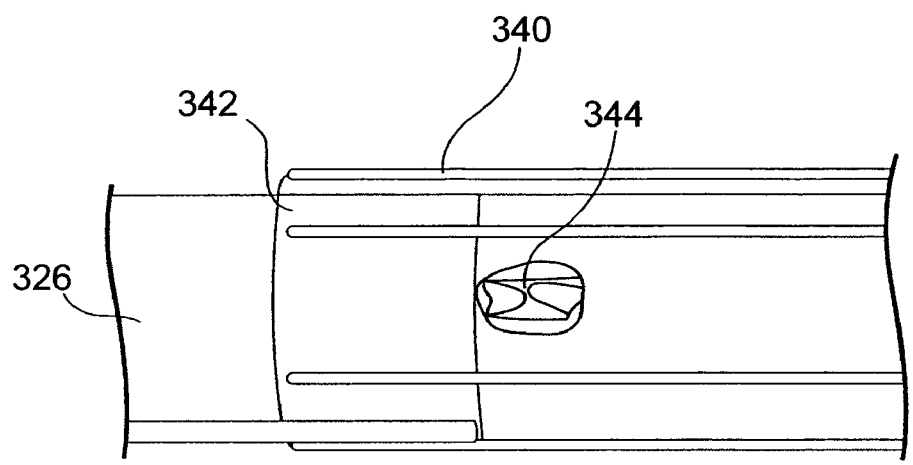
Figure 31:
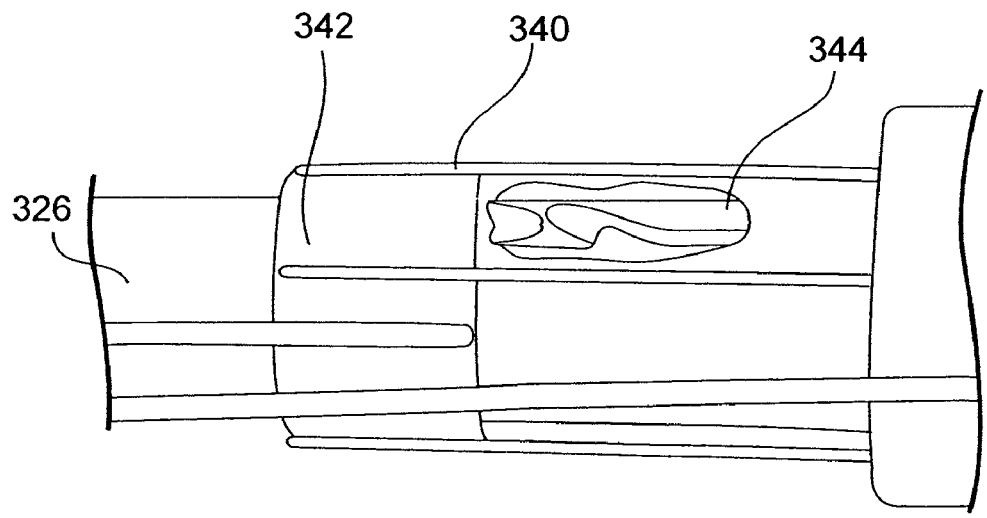

FIGS. 30-31 illustrate a method of retracting urethral tines 340, which are arranged about a hub 342. In particular, a revision tool is inserted within tube 326, and when the tool is in the correct position, cutting mechanism 344 is used to penetrate tube 326 at the desired place relative to the tines 340. The revision tool is then moved relative to tube 326 so that cutting mechanism 244 will push the hub 340 in essentially an opposite direction from that described above relative to FIGS. 28 and 29, thereby retracting the urethral tines.

The present invention has now been described with reference to several embodiments thereof. The various embodiments described herein are not necessarily limited to male-oriented or related surgical procedures and may be applied to either gender and possibly to animals. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

The invention claimed is:

1. A surgical tool comprising:
   an elongated body having a proximal end, a distal end, and an outer surface extending between the proximal end and the distal end;
   first and second sets of tissue approximating structures having deployed and retracted positions relative to the elongated body;

an actuating mechanism extending from the proximal end of the elongated body for independently deploying and retracting each of the first and second sets of tissue approximating structures;

a drainage lumen extending from a drainage aperture at the distal end of the elongated body to the proximal end;

a main balloon adjacent to the distal end of the elongated body; and a strap connector extending from the outer surface of the elongated body and comprising an aperture;

a stabilization strap extending through the aperture of the strap connector; wherein one face of the stabilization strap comprises a removably attachable auxiliary strap for attaching the stabilization strap to the elongated body; wherein the auxiliary strap extends through the aperture of the strap connector.

2. The surgical tool of claim 1, wherein the stabilization strap is slideable relative to the strap connector aperture.

3. The surgical tool of claim 1, wherein the stabilization strap comprises a first end that is attachable to an opposite second end for securing the strap around the leg of a patient.

4. The surgical tool of claim 3, wherein the first end of the stabilization strap comprises a hook material and the second end of the stabilization strap comprises a mating loop material so that the first and second ends are removably attachable to each other.

* * * * *